US006414483B1

(12) United States Patent
Nath et al.

(10) Patent No.: US 6,414,483 B1

(45) Date of Patent: Jul. 2, 2002

(54) EDDY CURRENT INSPECTION METHOD AND APPARATUS FOR DETECTING FLAWS IN AN ELECTRICALLY CONDUCTIVE COMPONENT

(75) Inventors: Shridhar Champaknath Nath, Niskayuna; Thomas James Batzinger, Burnt Hills; Curtis Wayne Rose, Mechanicville; Paul Peter Stryjek, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 6 days.

(21) Appl. No.: 09/627,049

(22) Filed: Jul. 27, 2000

(51) Int. Cl.[7] .......................... G01N 27/82; G01N 27/90

(52) U.S. Cl. ........................ 324/232; 324/238; 324/242; 324/262

(58) Field of Search ................................ 324/232, 234, 324/236–243, 261, 262

(56) References Cited

U.S. PATENT DOCUMENTS

| | | | | |
|---|---|---|---|---|
| 4,706,020 A | * 11/1987 | Viertl et al. | 324/238 |
| 4,799,010 A | * 1/1989 | Muller | 324/232 X |
| 5,047,719 A | * 9/1991 | Johnson et al. | 324/242 |
| 5,485,084 A | * 1/1996 | Duncan et al. | 324/242 X |
| 5,659,248 A | * 8/1997 | Hedengren et al. | 324/232 X |
| 5,966,011 A | * 10/1999 | Goldfine et al. | 324/243 X |

FOREIGN PATENT DOCUMENTS

| | | | |
|---|---|---|---|
| CH | 673896 | * 4/1990 | 324/242 |
| GB | 886247 | * 1/1962 | 324/238 |

* cited by examiner

*Primary Examiner*—Gerard R. Strecker

(74) *Attorney, Agent, or Firm*—V. Ramaswamy; Senniger, Powers, Leavitt & Roedel

(57) ABSTRACT

A method of inspecting a preselected area of an electrically conductive component to determine whether flaws are present. The method includes the steps of permanently mounting an eddy current element on the component over the preselected area and energizing the element to generate alternating magnetic fields proximate the component. An electrical signal generated by a secondary magnetic field formed proximate the component is detected using the element and the detected electrical signal is compared to a reference signal to determine whether the detected signal is different than the reference signal. Differences indicate the presence of a flaw in the component. Inspection apparatus for performing this method is also disclosed.

12 Claims, 3 Drawing Sheets

EDDY CURRENT INSPECTION METHOD AND APPARATUS FOR DETECTING FLAWS IN AN ELECTRICALLY CONDUCTIVE COMPONENT

BACKGROUND OF THE INVENTION

The present invention relates generally to eddy current inspection, and more particularly to components having permanently affixed eddy current elements.

Eddy current inspection is commonly used to detect flaws in electrically conductive components such as aluminum aircraft fuel tanks. Electromagnetic induction is used in this type of inspection to induce eddy currents in the component being inspected. Generally, a probe having one or more coils is used to generate alternating magnetic fields which induce the eddy currents in the component. When flaws are present in the component, the flow of eddy currents is altered. The altered eddy currents produce changes in a secondary magnetic field which are detected by the probe. The probe generates an electrical signal in response to the altered secondary magnetic field. The amplitude and phase of the electrical signal is generally proportionate to the size of the flaw.

As previously mentioned, a probe having one or more coils was used in the past to perform the inspections. The probe was positioned adjacent to the surface being inspected. Using a probe to inspect interior surfaces of components such as bulkheads forming fuel tanks inside aircraft wings required disassembly of the structure to position the probe adjacent the surface. Depending upon the complexity of the structure, disassembly, inspection and reassembly can take several hours, days, weeks or longer. During this time, the structure is unavailable. Further, the cost of labor required to perform these tasks can be high. Accordingly, a need exists for a method and apparatus for performing eddy current inspection of interior surfaces of complex structures without disassembling the structures.

SUMMARY OF THE INVENTION

Among the several features of the present invention may be noted the provision of a method of inspecting a preselected area of an electrically conductive component to determine whether flaws are present therein. The method comprises the steps of permanently mounting an eddy current element on the component over the preselected area and energizing the element to generate alternating magnetic fields proximate the component thereby inducing eddy currents in the component. An electrical signal generated by a secondary magnetic field formed proximate the component by the eddy currents is detected by the element, and the detected electrical signal is compared to a reference signal to determine whether the detected signal is different than the reference signal. A difference indicates a flaw is present in the component.

In another aspect, a method of the present invention for installing inspection apparatus on a component comprises permanently mounting an eddy current element on the component and attaching a conduit to the component. A lead is attached to the eddy current element and threaded through the conduit for selectively connecting the eddy current element to remote eddy current inspection equipment.

In still another aspect, the present invention includes inspection apparatus for detecting flaws in a preselected area of an electrically conductive component. The apparatus includes a substrate sized and shaped for covering the preselected area of the component. The substrate includes an adhesive for attaching the substrate to the component over the preselected area. Further, the apparatus includes a primary eddy current element mounted on the substrate sized and shaped for covering at least a portion of the preselected area to detect flaws in the component.

Yet another aspect of the present invention includes an electrically conductive component having an area selected for inspection in combination with apparatus for detecting flaws in the selected area of the component. The apparatus comprises a substrate mounted on the component over the area selected for inspection and a primary eddy current element mounted on the substrate over at least a portion of the selected area for detecting flaws in the area.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
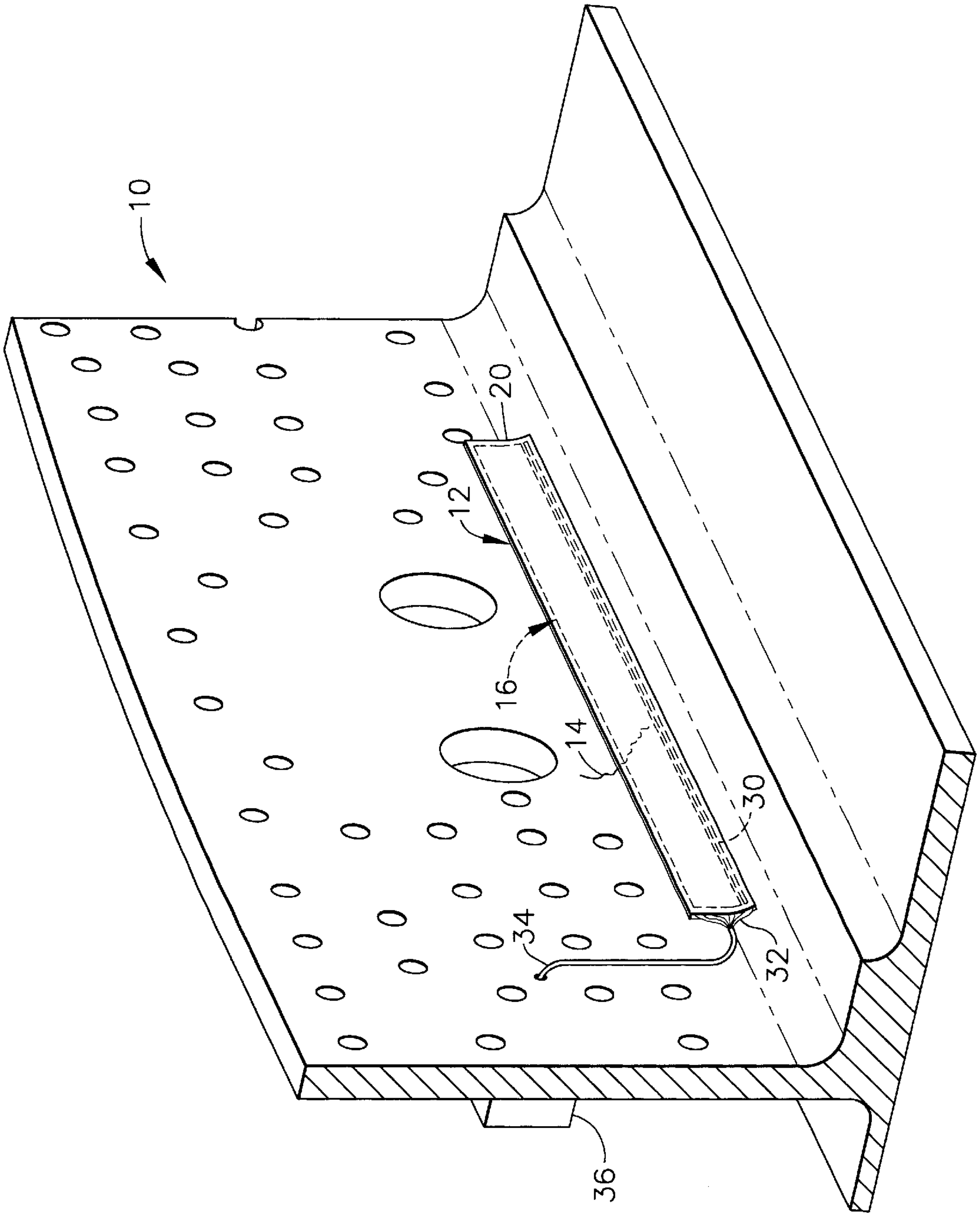
FIG. 1 is a fragmentary perspective of a component having inspection apparatus of the present invention.

Referring now to the drawings and in particular to FIG. 1, a electrically conductive component such as a portion of a bulkhead used to form an aircraft fuel tank is generally designated by the reference number 10. The component 10 is conventional in all respects and will not be described in further detail.

As further illustrated in FIG. 1, inspection apparatus (generally designated by 12) is mounted on the component 10 for detecting flaws (e.g., a crack 14) in a preselected area 16 of the component. Although only a small portion of the component 10 is covered by the apparatus 12 in FIG. 1, those skilled in the art will appreciate that the apparatus may be positioned over each critical portion of the component or those portions which are particularly susceptible to failure. Further, the entire component 10 (or those portions which are inspectible by eddy current inspection) may be covered by the apparatus 12 without departing from the scope of the present invention.

Figure 2:
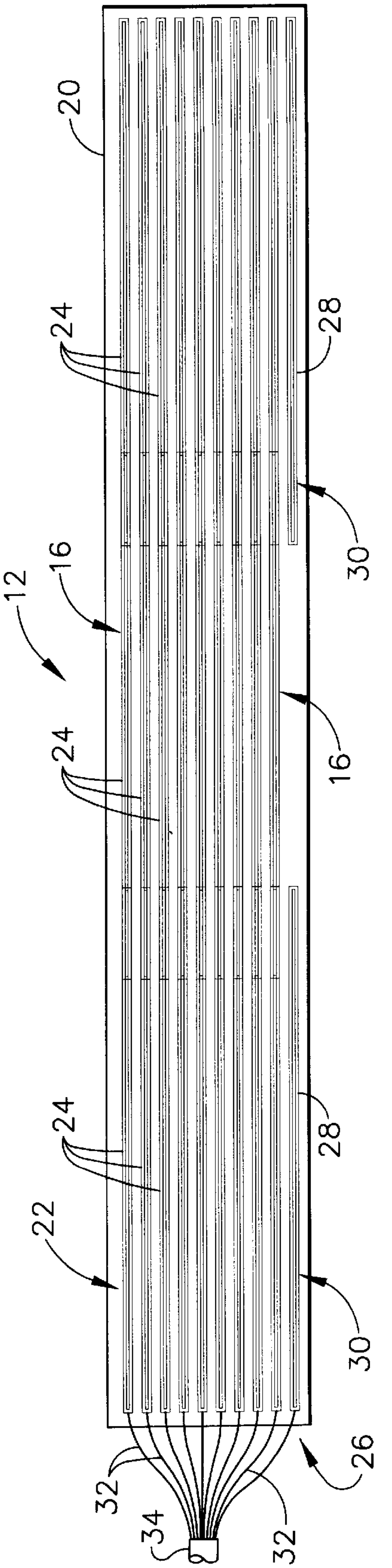
FIG. 2 is a front elevation of inspection apparatus of the present invention.

As illustrated in FIG. 2, the apparatus 12 includes a substrate 20 sized and shaped for covering the preselected area 16 of the component 10. Although the substrate may have other sizes and shapes without departing from the scope of the present invention, the substrate 20 of the preferred embodiment is rectangular, having a width of about 12.5 mm and a length of about 112.5 mm. Further, although the substrate may be made of other materials without departing from the scope of the present invention, the substrate 20 of the preferred embodiment is a sheet of Kapton tape having an adhesive backing for attaching the substrate to the component 10 over the preselected area 16. Kapton is a U.S. federally registered trademark of E. I. du Pont de Nemours and Company of Wilmington, Del.

Alternatively, a separate adhesive tape (not shown) may be used to attach the substrate 20 to the component 10.

A primary eddy current element, generally designated by 22, comprising several eddy current coils 24 is mounted on the substrate 20 (FIG. 2). Although other numbers and patterns of primary coils 24 may be used without departing from the scope of the present invention, the primary element 22 of the preferred embodiment has an array of coils formed by nine rows of coils containing three overlapping coils each. Although other coil sizes and shapes may be used without departing from the scope of the present invention, each of the coils of the preferred embodiment is rectangular, having a width of about 0.75 mm and a length of about 42.5 mm. Thus, the element 22 of the preferred embodiment is sized and shaped for covering at least a portion of the preselected area 16 to detect flaws in the component. Further, the coils 24 in each row of the preferred embodiment are overlapped by a distance of about 7.5 mm. Although the coils may be made of other materials and by other processes without departing from the scope of the present invention, the coils of the preferred embodiment are copper and are etched in the substrate by a conventional photolithographic process.

As further illustrated in FIG. 2, a reference eddy current element 26 comprising eddy current coils 28 is mounted on the substrate 20 below the lowermost row of primary eddy current coils 24. As will be appreciated by those skilled in the art, since both the primary eddy current element 22 and the reference eddy current element 26 are spaced from the component 10 by the substrate 20, these elements are spaced from the component by a substantially equal and constant distance (i.e., the thickness of the substrate). Although other numbers and patterns of reference coils may be used without departing from the scope of the present invention, the reference element 26 of the preferred embodiment has two separated coils 28 positioned over a reference area 30 (FIG. 1) of the component 10 located outside the area selected for inspection 16. Preferably, the reference element 26 is positioned so it obtains a reference signal corresponding to a portion of the component 10 without flaws. Alternatively, it is envisioned that the primary coils 24 may be scanned for a coil producing a nominal signal and that coil can be used as a reference coil. Thus, under some circumstances the reference element may be located inside the selected area 16 rather than outside of it.

Instrumentation leads 32 are connected to each primary coil 24 and each reference coil 28 as shown in FIG. 2. These leads 32 are bundled and fed through a protective tube or conduit 34 leading to an electrical connector 36 (FIG. 1) positioned for access by technicians to selectively connect the primary element 22 and reference element 26 to conventional eddy current equipment (generally designated by 40 in FIG. 3). Although the tube 34 may have other configurations without departing from the scope of the present invention in one preferred embodiment the tube is a cylindrical tube having an outer diameter of about 5 mm. Further, although other means of attaching the the 34 to the component may be used without departing from the scope of the present invention, in one embodiment the tube is attached to the component with a suitable conventional adhesive. Holes and/or grooves or other openings may be formed in low stress regions of the component 10 to accommodate the tube 34. Further, the ends of the tube 34 may be sealed with a suitable conventional sealant to prevent contaminates from entering the tube and component 10. Still further, it is envisioned that openings may be formed in the side of the tube 34 to provide access for the leads 32.

As will be appreciated by those skilled in the art, the apparatus 12 described above may be used to inspect a preselected area 16 of an electrically conductive component 10 to determine whether flaws (e.g., a crack 14) are present. First an eddy current element 22 is permanently mounted on the component 10 over the preselected area 16. When the preselected area is tested, conventional eddy current equipment 40 is connected to the element 22 using the connector 36. The equipment 40 energizes the element 22 to generate alternating magnetic fields proximate the component 10 thereby inducing eddy currents in the component. As will be understood by those skilled in the art, the element 22 detects an electrical signal generated by a secondary magnetic field formed proximate the component 10 by the eddy currents. The detected electrical signal is compared to a reference signal to determine whether the detected signal is different than the reference signal. Such a difference indicates the presence of a flaw 14 in the component 10.

Figure 3:
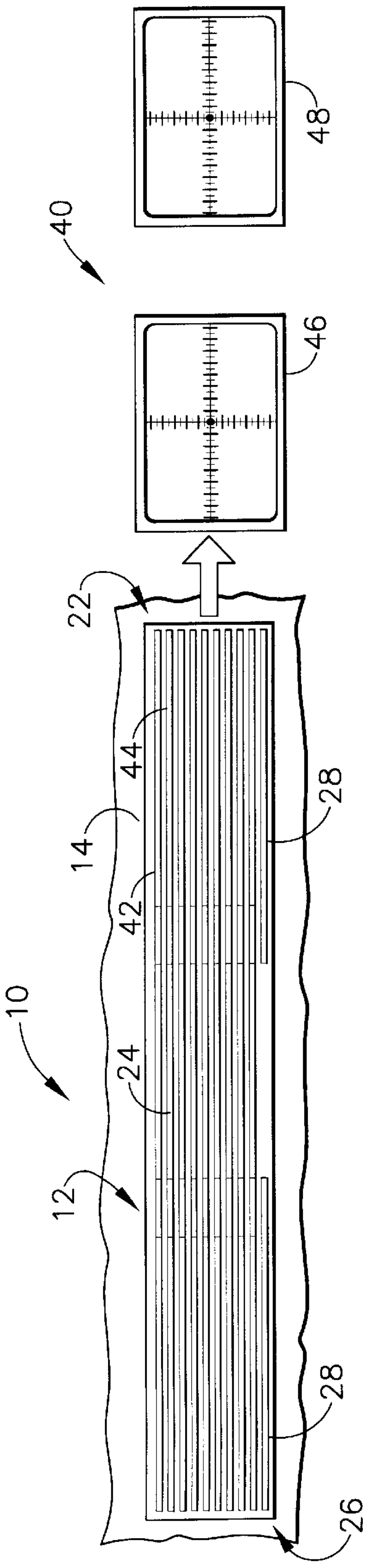
FIG. 3 is a schematic showing the inspection apparatus and a response from eddy current equipment for a component having no flaws.
Figure 4:
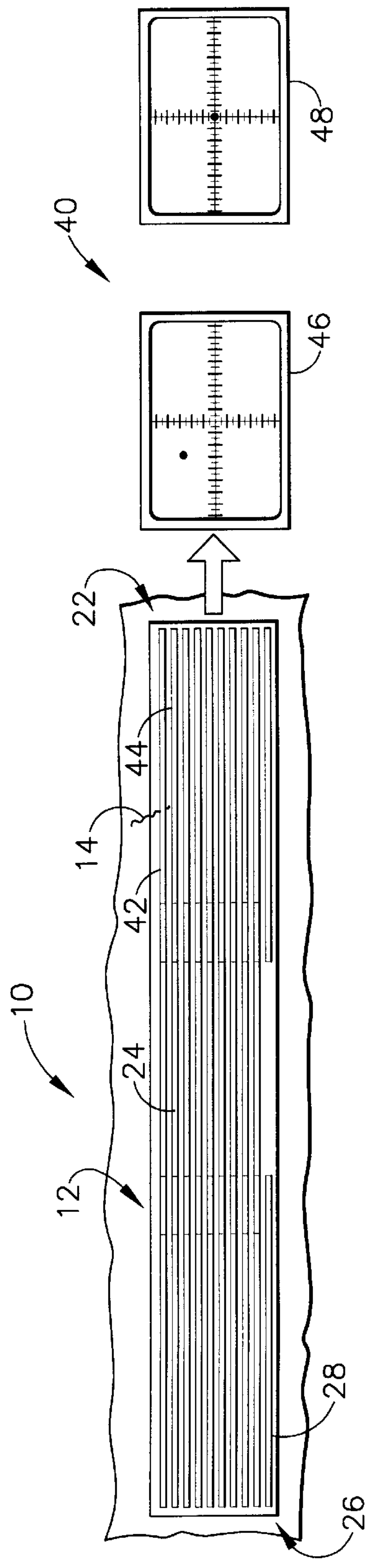
FIG. 4 is a schematic showing the apparatus and response for a component having a small flaw.
Figure 5:
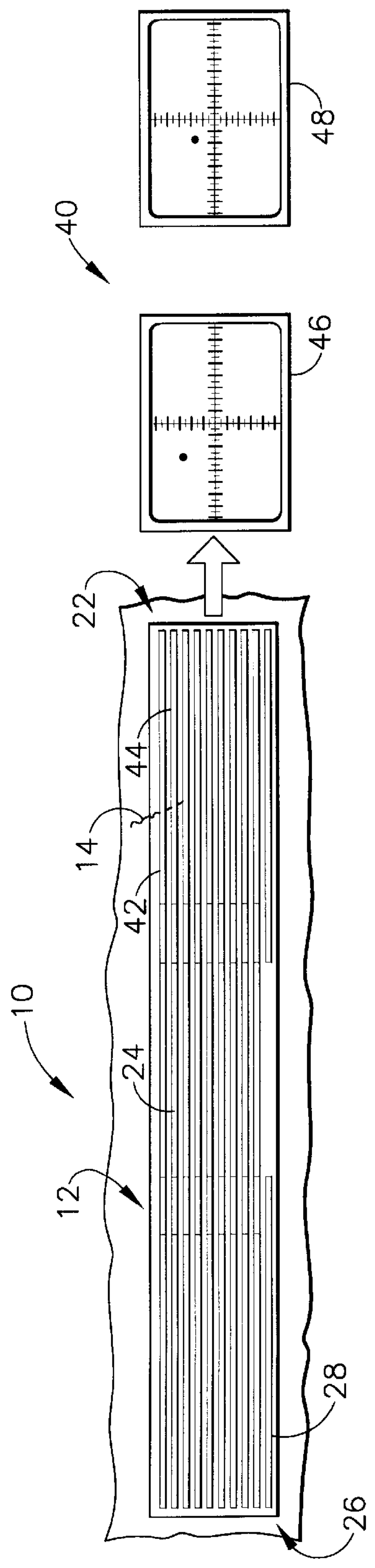
FIG. 5 is a schematic showing the apparatus and response for a component having a larger flaw.

As illustrated in FIG. 3, if no flaws are present the electrical signals received by the primary coils (e.g., coils 42, 44) are equal to the reference signals received by the reference coils 28. Thus, when the impedance of coil 42 is compared to the impedance of the reference coils 28 on a corresponding display 46 of the eddy current equipment 40, the difference is zero. Likewise, when the impedance of coil 44 is compared to the impedance of the reference coils 28 on a corresponding display 48 of the eddy current equipment 40, the difference is zero. However, when a flaw such as a crack 14 grows to a length as shown in FIG. 4, the display 46 shows a difference in impedance between coil 42 and coils 28. Since the length of the flaw does not extend under the coil 44, the corresponding display 48 displays a null reading. As the crack grows longer as shown in FIG. 5, displays 46 and 48 both show a difference in impedance between the respective coils. Thus, the location and the length of any flaws may be detected using the apparatus 12 and method described above.

When introducing elements of the present invention or the preferred embodiment(s) thereof, the articles “a”, “an”, “the” and “said” are intended to mean that there are one or more of the elements. The terms “comprising”, “including” and “having” are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method of inspecting a preselected area of an electrically conductive component to determine whether flaws are present therein, the method comprising:

permanently mounting an eddy current element comprising a plurality of eddy current coils arranged in an array on the component over the preselected area, each of said plurality of eddy current coils being located at a predetermined position within the array so that each of said coils is positioned at a predetermined location in the preselected area of the component when the element is mounted thereto;

attaching a conduit to the component;

attaching a lead to the eddy current element for selectively connecting she eddy current element to remote eddy current inspection equipment;

threading the lead through the conduit;

energizing the element to generate alternating magnetic fields proximate the component thereby inducing eddy currents in the component;

detecting with each of said plurality of coils in the element an electrical signal generated by a secondary magnetic field formed proximate the component by the eddy currents induced by the element; and comparing the electrical signal detected by each of said plurality of coils in the element to a reference signal to determine whether the detected signal is different than the reference signal thereby indicating presence of a flaw in the component at a particular location within the component generally corresponding to the predetermined location of the coil being compared.

2. A method as set forth in claim 1 wherein:

the eddy current element is permanently mounted on the component before the component is operated for a period of operation;

the element is energized after the period of operation;

the electrical signal detected by each of said plurality of coils in the element is compared to the reference signal after the period of operation.

3. A method as set forth in claim 1 further comprising the steps of:

forming an opening in the component adapted for receiving the conduit; and positioning the conduit in the opening.

4. A method as set forth in claim 1 further comprising the step of sealing the conduit to prevent contaminates from passing therethrough.

5. Inspection apparatus for detecting flaws in a preselected area of an electrically conductive component, said apparatus comprising:

a substrate sized and shaped for covering the preselected area of the component, said substrate including an adhesive for attaching the substrate to the component over the preselected area;

a primary eddy current element comprising a plurality of eddy current coils mounted on the substrate, said plurality of coils being arranged in an array sized and shaped for covering at least a portion of the preselected area to detect flaws in the component and to determine the locations of the flaws; and a reference eddy current element mounted on the substrate adjacent the primary eddy current element for obtaining a reference signal corresponding to a portion of the component without flaws.

6. In combination, an electrically conductive component having an area selected for inspection and apparatus for detecting flaws in the selected area of the component, said apparatus comprising:

a substrate mounted on the component over the area selected for inspection;

a primary eddy current element mounted on the substrate over at least a portion of the selected area for detecting flaws in the area, said primary eddy current element comprising a plurality of eddy current coils arranged in a preselected pattern, each of said plurality of eddy current coils being located at a predetermined position on the substrate so that each of said coils is positioned at a predetermined location in the area of the component selected for inspection; and a reference eddy current element mounted on the substrate adjacent the primary eddy current element for obtaining a reference signal corresponding to a portion of the component without flaws.

7. A combination as set forth in claim 6 wherein the reference eddy current element is positioned over a reference area of the component located outside the area selected for inspection.

8. A combination as set forth in claim 6 wherein:

each coil within the plurality of coils of the primary eddy current element is spaced from the component by a substantially constant distance; and the reference eddy current element is spaced from the component by the distance.

9. A combination as set forth in claim 6 wherein the substrate is adhesively bonded to the component over the area selected for inspection.

10. A combination as set forth in claim 6 further comprising an electrical connector mounted on the component for selectively connecting the primary eddy current element to remote eddy current inspection equipment.

11. A combination as set forth in claim 6 wherein said plurality of eddy current coils in the primary eddy current element are mounted on the substrate over substantially all of the selected area.

12. A combination as set forth in claim 6 further comprising:

a conduit mounted on the component; and a lead extending through the conduit from the eddy current element for selectively connecting the eddy current element to remote eddy current inspection equipment.

* * * * *